(12) United States Patent
Matsumoto et al.

(10) Patent No.: US 11,983,896 B2
(45) Date of Patent: May 14, 2024

(54) LINE-OF-SIGHT DETECTION APPARATUS AND LINE-OF-SIGHT DETECTION METHOD

(71) Applicant: Mitsubishi Electric Corporation, Tokyo (JP)

(72) Inventors: Atsushi Matsumoto, Tokyo (JP); Hirotaka Sakamoto, Tokyo (JP); Shusaku Takamoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 523 days.

(21) Appl. No.: 17/282,478

(22) PCT Filed: Oct. 9, 2018

(86) PCT No.: PCT/JP2018/037529
§ 371 (c)(1),
(2) Date: Apr. 2, 2021

(87) PCT Pub. No.: WO2020/075215
PCT Pub. Date: Apr. 16, 2020

(65) Prior Publication Data
US 2021/0383566 A1 Dec. 9, 2021

(51) Int. Cl.
*G06V 40/18* (2022.01)
*G06T 7/73* (2017.01)
(Continued)

(52) U.S. Cl.
CPC .............. *G06T 7/73* (2017.01); *G06V 20/597* (2022.01); *G06V 40/161* (2022.01);
(Continued)

(58) Field of Classification Search
CPC ............ G06T 7/73; G06T 2207/30201; G06T 2207/30268; G06V 20/597; G06V 40/161;
(Continued)

(56) References Cited

U.S. PATENT DOCUMENTS

| 8,891,819 B2 | 11/2014 | Kaneda et al. |
| 2012/0189160 A1* | 7/2012 | Kaneda .................. G06V 40/19 348/207.99 |

FOREIGN PATENT DOCUMENTS

| JP | 2005-66023 A | 3/2005 |
| JP | 4826506 B2 | 11/2011 |
| JP | 5618686 B2 | 11/2014 |

OTHER PUBLICATIONS

International Search Report, issued in PCT/JP2018/037529, PCT/ISA/210, dated Jan. 15, 2019.

* cited by examiner

*Primary Examiner* — Huy C Ho
(74) *Attorney, Agent, or Firm* — Birch, Stewart, Kolasch & Birch, LLP

(57) ABSTRACT

Provided is a line-of-sight detection apparatus that outputs reliability of an estimation result of a line of sight when an eye to be a line-of-sight detection target is switched. The line-of-sight detection apparatus includes: an estimation target selection unit configured to select an eye of a line-of-sight detection target person as one of switchable line-of-sight detection modes; a line-of-sight estimation unit configured to estimate a line of sight of the line-of-sight detection target person in the line-of-sight detection mode; a reliability determination unit configured to determine, based on a first line of sight before the mode is switched and a second line of sight after the mode is switched, reliability of the second line of sight; and a line-of-sight direction
(Continued)

output unit configured to output information on the second line of sight and the reliability of the second line of sight.

10 Claims, 13 Drawing Sheets

(51) Int. Cl.
*G06V 20/59* (2022.01)
*G06V 40/16* (2022.01)

(52) U.S. Cl.
CPC ............ *G06V 40/171* (2022.01); *G06V 40/18* (2022.01); *G06T 2207/30201* (2013.01); *G06T 2207/30268* (2013.01)

(58) Field of Classification Search
CPC ...... G06V 40/171; G06V 40/18; G06V 40/19; A61B 3/113
USPC ......................................................... 382/103
See application file for complete search history.

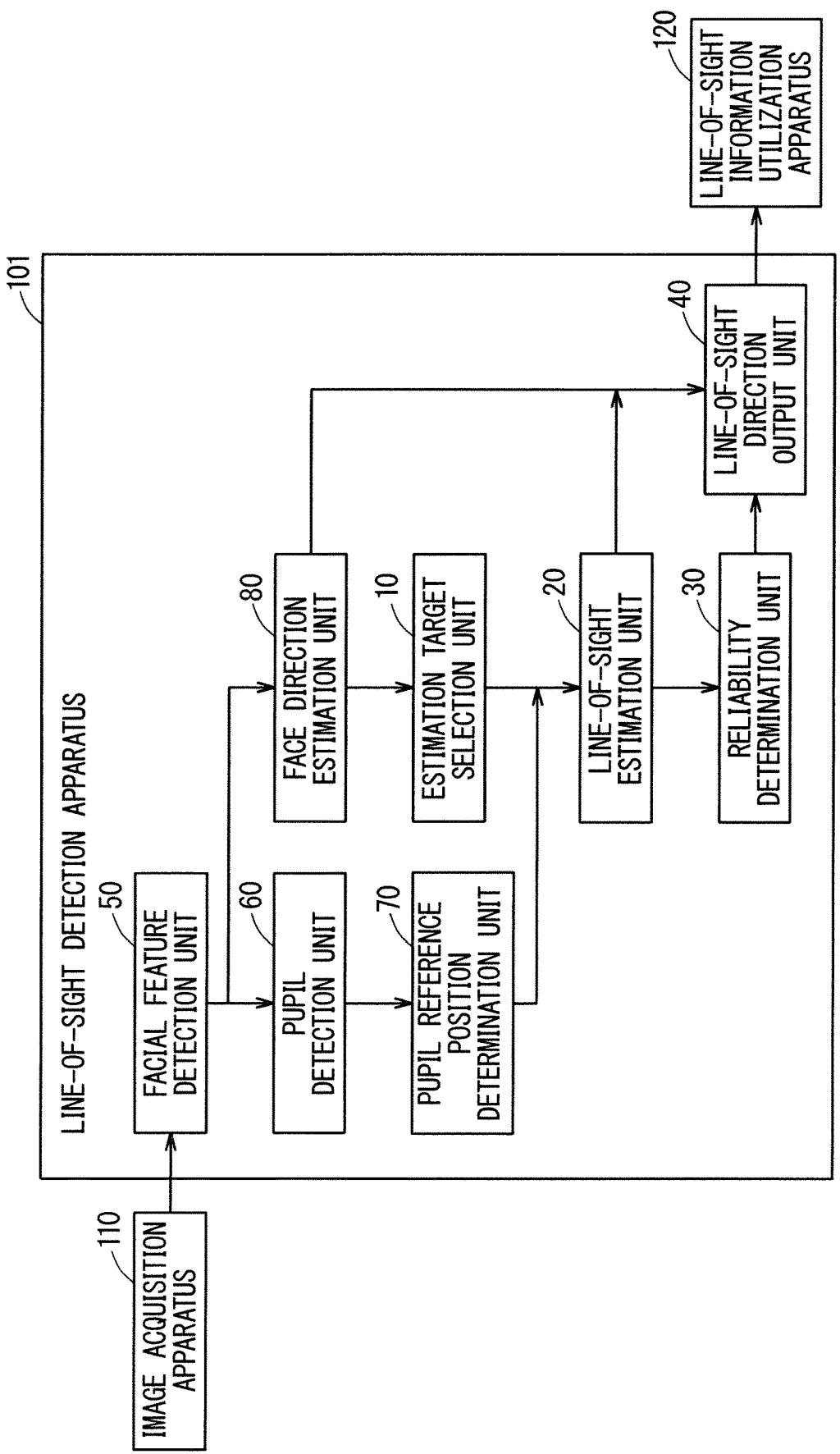
F I G. 5

LINE-OF-SIGHT DETECTION APPARATUS AND LINE-OF-SIGHT DETECTION METHOD

TECHNICAL FIELD

The present invention relates to a line-of-sight detection apparatus and a line-of-sight detection method.

BACKGROUND ART

Patent Document 1 discloses a driver state detection apparatus. The driver state detection apparatus detects the reference position of the driver's eyes and determines the driver's visual recognition region based on the reference position. The driver state detection apparatus achieves highly accurate detection regardless of personal characteristics such as the driver's physique.

Patent Document 2 discloses a line-of-sight detection apparatus. Conventionally, the line-of-sight detection accuracy has been lowered when one eye is hidden by turning the face sideways or the eyes are hidden by being covered with hair. In order to solve such a problem, the line-of-sight detection apparatus described in Patent Document 2 includes a piece of means for selecting the eye to be used for line-of-sight estimation (left eye only, both eyes, and right eye only) depending on the degree of eye expression or the reliability expressed by the direction of the face. By estimating the line of sight of the selected eye, the line-of-sight detection apparatus enables highly accurate line-of-sight detection even when eye hiding occurs.

PRIOR ART DOCUMENTS

Patent Documents

Patent Document 1: Japanese Patent Application Laid-Open No. 2005-66023
Patent Document 2: Japanese Patent No. 5618686

SUMMARY

Problem to be Solved by the Invention

When the line of sight direction of the driver is estimated with a camera mounted near the center console of the vehicle, the image of the eye farther from the camera (for example, the driver's right eye when the driver of a right-hand drive vehicle is the target of line-of-sight detection) is captured smaller. In addition, depending on the direction of the face, the eyes may be hidden from the camera. In such a case, the detection accuracy of the line of sight is lowered. Therefore, it is appropriate that the line-of-sight direction is detected by the eye closer to the camera. Further, calculating the line of sight based on the information on the eye closer to the camera also allows the amount of calculation at the time of line-of-sight detection to be reduced.

When the face direction of the driver changes during driving and the eye closer to the camera switches, the eye to be the target of line-of-sight estimation is switched. For example, when the driver of a right-hand drive vehicle turns his face toward the side mirror on the passenger seat side while driving facing the front, the eye to be the target of line-of-sight estimation is switched from the left eye to the right eye. Even if the eye to be the target of line-of-sight estimation is switched, it is expected that the line-of-sight estimation direction will change continuously before and after the switching. However, if the characteristics of the driver's left eye and right eye are different, the line of sight may not change continuously. Discontinuous changes may cause erroneous decision on line-of-sight estimation.

The present invention has been made to solve the above problems and has an object to provide a line-of-sight detection apparatus that outputs the reliability of the estimation result of the line of sight before and after the switching when the switching of an eye to be the target of line-of-sight detection occurs.

Means to Solve the Problem

The line-of-sight detection apparatus according to the present invention includes: an estimation target selection unit configured to select an eye to be a line-of-sight estimation target of a line-of-sight detection target person as one line-of-sight detection mode in a plurality of switchable line-of-sight detection modes; a line-of-sight estimation unit configured to estimate a line of sight of the line-of-sight detection target person in the one line-of-sight detection mode; a reliability determination unit configured to determine, based on a first line of sight that is the line of sight before the line-of-sight detection mode is switched by selection of the estimation target selection unit and a second line of sight that is the line of sight after the line-of-sight detection mode is switched, reliability of the second line of sight after the line-of-sight detection mode is switched; and a line-of-sight direction output unit configured to output information on the second line of sight and the reliability of the second line of sight.

Effects of the Invention

According to the present invention, it is possible to provide a line-of-sight detection apparatus that outputs the reliability of the estimation result of the line of sight before and after the switching when the eye to be the line-of-sight detection target is switched.

The objects, features, aspects, and advantages of the present invention will become more apparent from the following detailed description and the accompanying drawings.

BRIEF DESCRIPTION OF DRAWINGS

FIG. 5 is a block diagram showing a configuration of a line-of-sight detection apparatus and apparatuses that operate in connection therewith according to the second embodiment.

DESCRIPTION OF EMBODIMENTS

First Embodiment (Configuration of Line-of-Sight Detection Apparatus)

Figure 1:
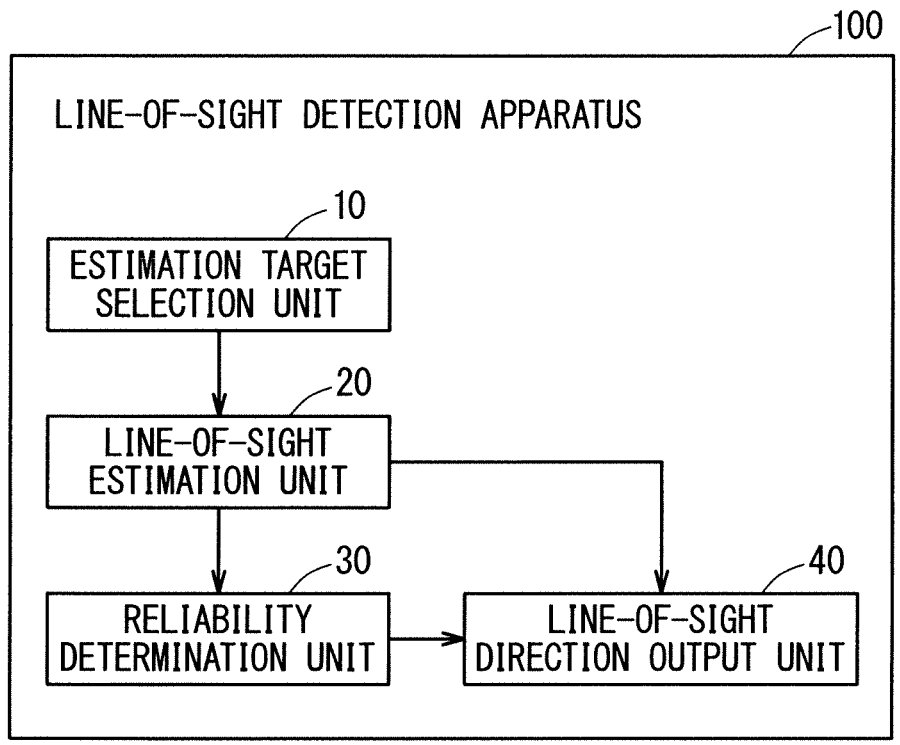
FIG. 1 is a block diagram showing a configuration of a line-of-sight detection apparatus according to the first embodiment.

FIG. 1 is a block diagram showing a configuration of a line-of-sight detection apparatus 100 according to the first embodiment.

The line-of-sight detection apparatus 100 includes an estimation target selection unit 10, a line-of-sight estimation unit 20, a reliability determination unit 30, and a line-of-sight direction output unit 40.

The estimation target selection unit 10 selects an eye to be a line-of-sight estimation target of a line-of-sight detection target person as one line-of-sight detection mode in a plurality of switchable line-of-sight detection modes. The line-of-sight detection target person is, for example, a crew of a vehicle. The crew of a vehicle is, for example, a driver. However, the line-of-sight detection target person is not limited to them. The eye to be the line-of-sight estimation target is the right eye, the left eye, or both eyes.

The line-of-sight estimation unit 20 estimates a line of sight of the line-of-sight detection target person in the line-of-sight detection mode selected by the estimation target selection unit. For example, when the line-of-sight detection mode is the right eye, the line-of-sight estimation unit 20 estimates a line of sight of the right eye of the line-of-sight detection target person. When the line-of-sight detection mode is the left eye, the line-of-sight estimation unit 20 estimates a line of sight of the left eye of the line-of-sight detection target person. When the line-of-sight detection mode is both eyes, the line-of-sight estimation unit 20 estimates lines of sight of both eyes of the line-of-sight detection target person.

Based on a first line of sight that is the line of sight before the line-of-sight detection mode is switched by the selection of the estimation target selection unit 10, and a second line of sight that is the line of sight after the line-of-sight detection mode is switched, the reliability determination unit 30 determines reliability of the second line of sight after the line-of-sight detection mode is switched. For example, when the line-of-sight detection mode is switched from the right eye to the left eye or from the left eye to the right eye, the reliability determination unit 30 determines the reliability of the second line of sight. Alternatively, for example, when the line-of-sight detection mode is switched from both eyes to one eye, or from one eye to both eyes, the reliability determination unit 30 determines the reliability of the second line of sight.

The line-of-sight direction output unit 40 outputs the information on the second line of sight estimated by the line-of-sight estimation unit 20 and the reliability of the second line of sight determined by the reliability determination unit 30.

Figure 2:
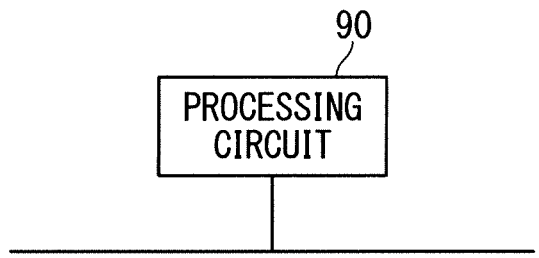
FIG. 2 is a diagram showing an example of a processing circuit included in the line-of-sight detection apparatus according to the first embodiment.

FIG. 2 is a diagram showing an example of a processing circuit 90 included in the line-of-sight detection apparatus 100. Each function of the estimation target selection unit 10, the line-of-sight estimation unit 20, the reliability determination unit 30, and the line-of-sight direction output unit 40 is achieved by the processing circuit 90. That is, the processing circuit 90 includes the estimation target selection unit 10, the line-of-sight estimation unit 20, the reliability determination unit 30, and the line-of-sight direction output unit 40.

When the processing circuit 90 is dedicated hardware, the processing circuit 90 is a single circuit, a composite circuit, a programmed processor, a parallel programmed processor, an application specific integrated circuit (ASIC), a field-programmable gate array (FPGA), a circuit that combines these, or the like, for example. Each function of the estimation target selection unit 10, the line-of-sight estimation unit 20, the reliability determination unit 30, and the line-of-sight direction output unit 40 may be achieved individually by a plurality of processing circuits, or may be achieved collectively by one processing circuit.

Figure 3:
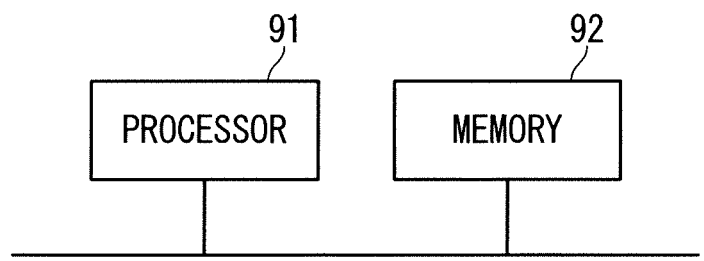
FIG. 3 is a diagram showing another example of a processing circuit included in the line-of-sight detection apparatus according to the first embodiment.

FIG. 3 is a diagram showing another example of a processing circuit included in the line-of-sight detection apparatus 100. The processing circuit includes a processor 91 and a memory 92. Executing the program stored in the memory 92 by the processor 91 allows each function of the estimation target selection unit 10, the line-of-sight estimation unit 20, the reliability determination unit 30, and the line-of-sight direction output unit 40 to be achieved. For example, each function is achieved by executing software or firmware described as a program by the processor 91. That is, the line-of-sight detection apparatus 100 includes a memory 92 for storing a program and a processor 91 for executing the program.

The program describes a function that the line-of-sight detection apparatus 100 selects an eye to be a line-of-sight estimation target of a line-of-sight detection target person as one line-of-sight detection mode in a plurality of switchable line-of-sight detection modes, estimate a line of sight of the line-of-sight detection target person in the one line-of-sight detection mode, determines, based on a first line of sight that is the line of sight before the line-of-sight detection mode is switched and a second line of sight that is the line of sight after the line-of-sight detection mode is switched, reliability of the second line of sight after the line-of-sight detection mode is switched, and outputs information on the second line of sight and the reliability of the second line of sight. In addition, the program causes the computer to execute the procedure or method of the estimation target selection unit 10, the line-of-sight estimation unit 20, the reliability determination unit 30, and the line-of-sight direction output unit 40.

The processor 91 is, for example, a central processing unit, a processing unit, an arithmetic unit, a microprocessor, a microcomputer, a digital signal processor (DSP), or the like. The memory 92 is a non-volatile or volatile semiconductor memory, such as a random-access memory (RAM), a read-only memory (ROM), a flash memory, an erasable programmable read-only memory (EPROM), or an electrically erasable programmable read-only memory (EEPROM). Alternatively, the memory 92 may be any storage medium to be used in the future, such as a magnetic disk, a flexible disk, an optical disc, a compact disc, a mini disc, or a DVD.

Some of the respective functions of the estimation target selection unit 10, the line-of-sight estimation unit 20, the reliability determination unit 30, and the line-of-sight direction output unit 40 described above may be achieved by dedicated hardware, and others may be achieved by software or firmware. Thus, the processing circuit achieves each of the above-described functions by hardware, software, firmware, or a combination thereof.

(Operation of Line-of-Sight Detection Apparatus and Line-of-Sight Detection Method)

Figure 4:
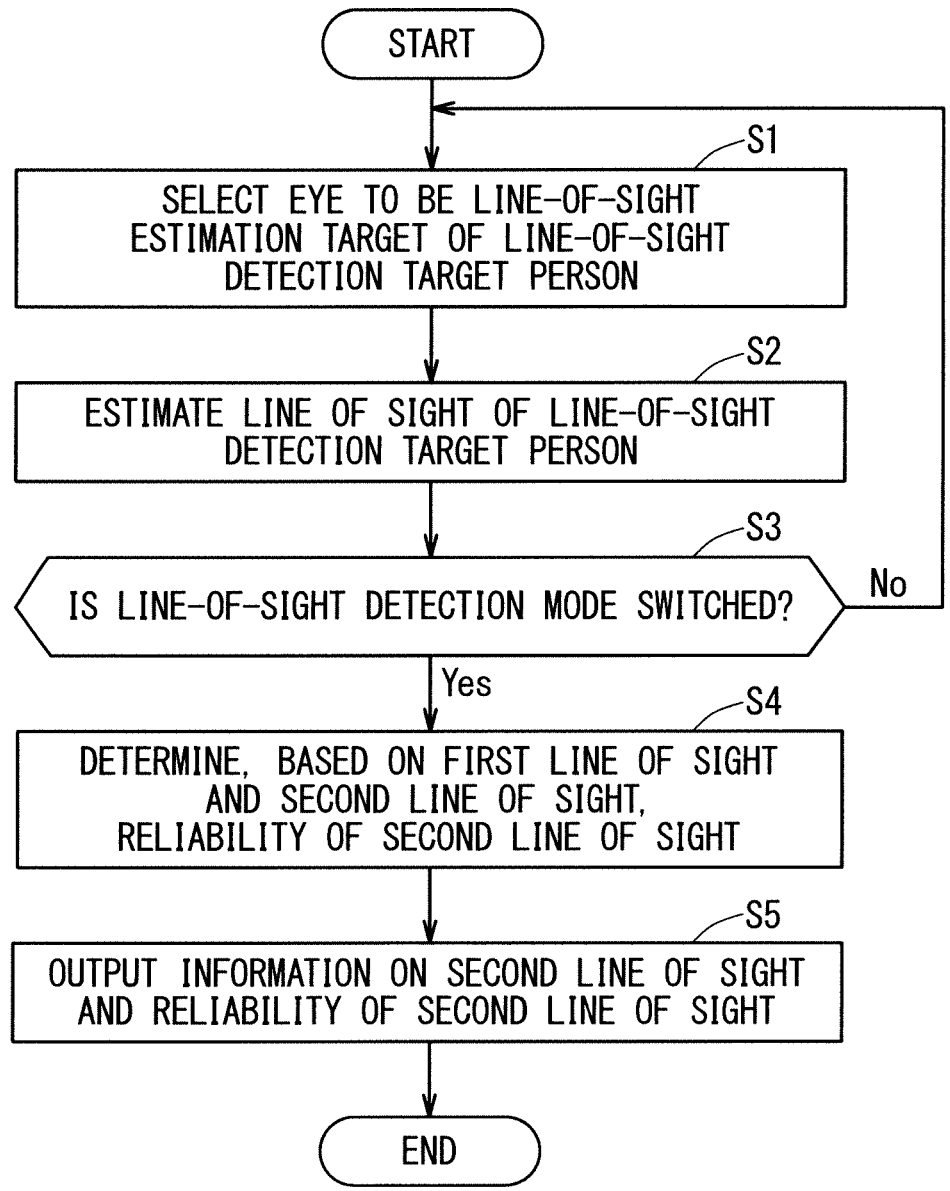
FIG. 4 is a flowchart showing an operation of the line-of-sight detection apparatus and a line-of-sight detection method according to the first embodiment.

FIG. 4 is a flowchart showing the operation of the line-of-sight detection apparatus 100 and the line-of-sight detection method according to the first embodiment.

In step S1, the estimation target selection unit 10 selects the eye to be the line-of-sight estimation target of the line-of-sight detection target person. That is, one line-of-sight detection mode is selected.

In step S2, the line-of-sight estimation unit 20 estimates the line of sight of the line-of-sight detection target person.

In step S3, the reliability determination unit 30 determines whether the line-of-sight detection mode has been switched. If the reliability determination unit 30 determines that the line-of-sight detection mode has been switched, step S4 is executed. If the reliability determination unit 30 determines that the line-of-sight detection mode has not been switched, step S1 is executed again.

In step S4, the reliability determination unit 30 determines, based on the first line of sight and the second line of sight, the reliability of the second line of sight.

In step S5, the line-of-sight direction output unit 40 outputs the information on the second line of sight and the reliability of the second line of sight.

Effect

To summarize the above, the line-of-sight detection apparatus 100 according the first embodiment includes: the estimation target selection unit 10 that selects an eye to be a line-of-sight estimation target of a line-of-sight detection target person as one line-of-sight detection mode in a plurality of switchable line-of-sight detection modes, the line-of-sight estimation unit 20 that estimates a line of sight of the line-of-sight detection target person in the one line-of-sight detection mode, the reliability determination unit 30 that determines, based on a first line of sight that is the line of sight before the line-of-sight detection mode is switched by the selection of the estimation target selection unit 10, and a second line of sight that is the line of sight after the line-of-sight detection mode is switched, reliability of the second line of sight after the line-of-sight detection mode is switched, and the line-of-sight direction output unit 40 that outputs information on the second line of sight and the reliability of the second line of sight.

With the above configuration, the line-of-sight detection apparatus 100 can output the reliability of the estimation results of the lines of sight before and after the switching when the switching of the eye to be the line-of-sight detection target occurs. The respective positions of the pupils of the left and right eyes depend on characteristics of an individual (for example, strabismus). When the line-of-sight detection mode is switched, the continuity of each line of sight before and after the switching may not be maintained. For example, if a system that determines the driver's inattentive driving uses the detection result of such a discontinuous line of sight, the determination of inattentive driving may be wrong. The line-of-sight detection apparatus 100 according to the first embodiment enables highly accurate line-of-sight detection by outputting the reliability of the line of sight when the line-of-sight detection mode is switched.

To summarize the above, the line-of-sight detection method according to the first embodiment includes selecting an eye to be a line-of-sight estimation target of a line-of-sight detection target person as one line-of-sight detection mode in a plurality of switchable line-of-sight detection modes, estimating a line of sight of the line-of-sight detection target person in the one line-of-sight detection mode, determining, based on a first line of sight that is the line of sight before the line-of-sight detection mode is switched and a second line of sight that is the line of sight after the line-of-sight detection mode is switched, reliability of the second line of sight after the line-of-sight detection mode is switched, and outputting information on the second line of sight and the reliability of the second line of sight.

With the above configuration, the line-of-sight detection method can output the reliability of the estimation results of the lines of sight before and after the switching when the switching of the eye to be the line-of-sight detection target occurs. The respective positions of the pupils of the left and right eyes depend on characteristics of an individual (for example, strabismus). When the line-of-sight detection mode is switched, the continuity of each line of sight before and after the switching may not be maintained. For example, if a system that determines the driver's inattentive driving uses the detection result of such a discontinuous line of sight, the determination of inattentive driving may be wrong. The line-of-sight detection method according to the first embodiment enables highly accurate line-of-sight detection by outputting the reliability of the line of sight when the line-of-sight detection mode is switched.

Second Embodiment

A line-of-sight detection apparatus and a line-of-sight detection method according to the second embodiment will be described. It should be noted that descriptions of configurations and operations similar to those in the first embodiment will be omitted.

(Configuration of Line-of-Sight Detection Apparatus)

FIG. 5 is a block diagram showing a configuration of a line-of-sight detection apparatus 101 and apparatuses that operate in connection therewith according to the second embodiment. FIG. 5 shows an image acquisition apparatus 110 and a line-of-sight information utilization apparatus 120 as apparatuses that operate in connection with the line-of-sight detection apparatus 101. The line-of-sight detection apparatus 101 detects the driver's line of sight based on the image of the driver of the vehicle acquired by the image acquisition apparatus 110.

Figure 6:
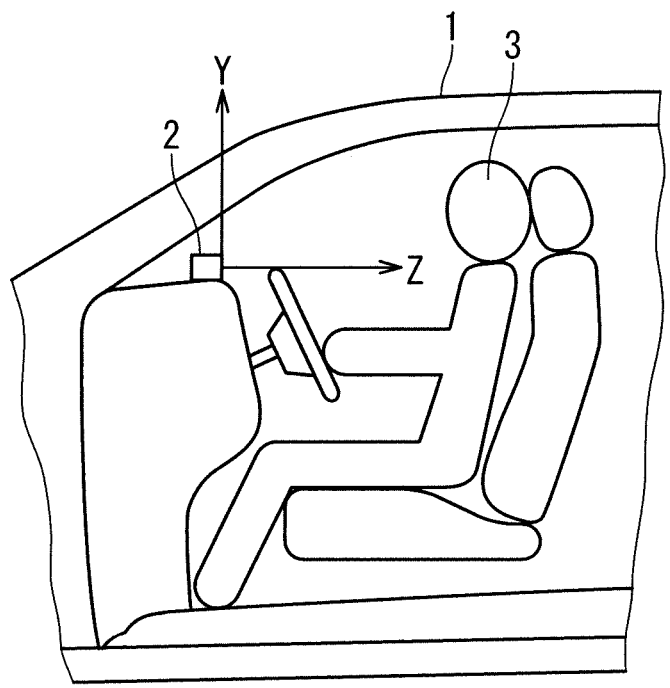
FIG. 6 is a diagram showing the inside of a vehicle according to the second embodiment.
Figure 7:
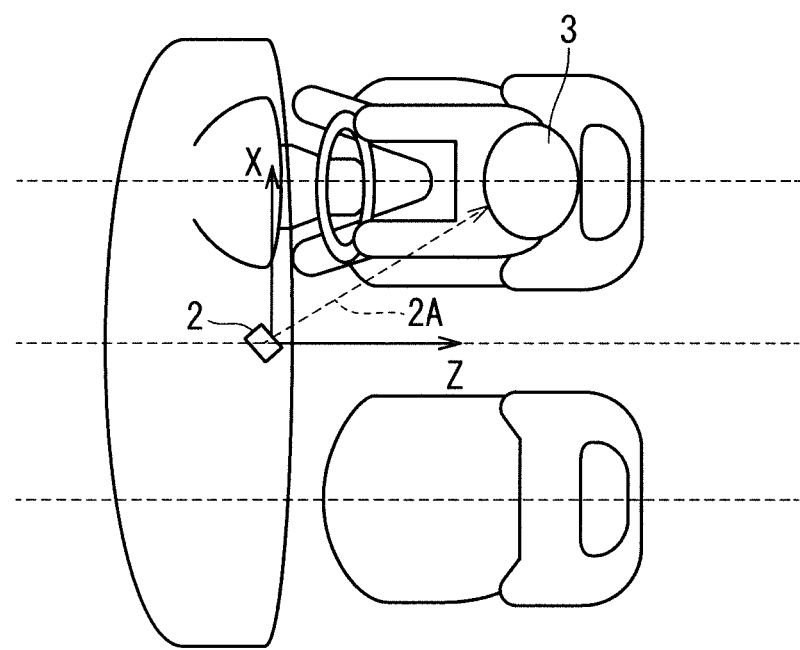
FIG. 7 is a diagram showing the inside of a vehicle according to the second embodiment.

The image acquisition apparatus 110 captures an image of a line-of-sight detection target person. The image acquisition apparatus 110 is, for example, a camera mounted on a vehicle. FIGS. 6 and 7 are views showing the inside of the vehicle 1. The camera 2 is installed at or near a center console in the front of the vehicle interior. Here, the vehicle 1 is a right-hand drive vehicle, and when the driver 3 that is the line-of-sight detection target person faces forward, the camera 2 is positioned in the left front. The camera 2 is arranged so that an image around the face of the driver 3 can be acquired. The camera 2 is installed so that the optical axis 2A of the camera 2 faces the driver's seat. However, the camera 2 may be provided with its optical axis 2A facing the Z-axis direction (the direction connecting the front and the rear of the vehicle 1). Since the optical axis 2A of the camera 2 faces the Z-axis direction, the camera 2 can capture both the driver 3 and the passenger in the passenger seat. In addition, the camera 2 continuously captures an image of the periphery of the face of the driver 3, that is, captures a video. Hereinafter, the image is an image for each frame constituting the video.

The facial feature detection unit 50 acquires an image of the line-of-sight detection target person from the image acquisition apparatus 110. The facial feature detection unit 50 detects facial features of the line-of-sight detection target person based on the image. The facial features are, for example, predetermined sites (positions of predetermined facial parts) such as organs constituting the face. The facial features are, for example, the positions of eyes.

The pupil detection unit 60 detects the pupil position based on the facial features, that is, the eye positions. The pupil position is the center position of the pupil with respect to the outer and inner corners of the eye in the facial image.

The pupil reference position determination unit 70 determines the pupil reference position that is the pupil position when the line-of-sight detection target person visually recognizes the front. Based on the assumption that the driver 3 faces approximately the front direction, that is, the front of the vehicle 1 while driving, the pupil reference position determination unit 70 obtains the frequency distribution of the pupil position from a plurality of images (a plurality of frames). Based on the frequency distribution, the pupil reference position determination unit 70 determines the pupil reference position when the driver 3 visually recognizes the front. It is preferable that the pupil reference position determination unit 70 prepare a frequency distribution of the pupil position based on an image in which the driver 3 visually recognizes the front direction. Therefore, the pupil reference position determination unit 70 may determine whether or not to adopt the detected pupil position as data for preparing the frequency distribution depending on the traveling state of the vehicle 1. The traveling state of the vehicle 1 is the speed or steering angle of the vehicle 1. For example, the pupil reference position determination unit 70 does not adopt the pupil position detected when the speed of the vehicle 1 is not more than a predetermined speed as data for preparing the frequency distribution. Alternatively, for example, the pupil reference position determination unit 70 does not adopt the pupil position detected with the steering wheel turned as data for preparing the frequency distribution.

The face direction estimation unit 80 estimates the direction of the face of the line-of-sight detection target person based on the facial features.

The estimation target selection unit 10 selects a line-of-sight detection mode based on the direction of the face of the line-of-sight detection target person. That is, the estimation target selection unit 10 selects the right eye, the left eye, or both eyes of the driver 3 as the line-of-sight detection mode.

The line-of-sight estimation unit 20 estimates a line of sight of the line-of-sight detection target person based on the difference between the pupil position in the line-of-sight detection mode selected by the estimation target selection unit 10 and the pupil reference position. For example, when the line-of-sight detection mode is one eye (right eye or left eye), the line-of-sight estimation unit 20 estimates the line of sight based on the difference between the pupil position of one eye and the pupil reference position. Alternatively, for example, when the line-of-sight detection mode is both eyes, the line-of-sight estimation unit 20 estimates each of the lines of sight of the right eye and the left eye based on the differences between the respective pupil positions and the pupil reference position of the right eye and the left eye. The position where the line of sight of the right eye and the line of sight of the left eye intersect is the position at which the line-of-sight detection target person gazes.

Based on the first line of sight that is the line of sight before the line-of-sight detection mode is switched by the selection of the estimation target selection unit 10, and the second line of sight that is the line of sight after the line-of-sight detection mode is switched, the reliability determination unit 30 determines reliability of the second line of sight after the line-of-sight detection mode is switched. For example, when the line-of-sight detection mode is switched from the right eye to the left eye or from the left eye to the right eye, the reliability determination unit 30 determines the reliability of the second line of sight. Alternatively, for example, when the line-of-sight detection mode is switched from one eye to both eyes, or from both eyes to one eye, the reliability determination unit 30 determines the reliability of the second line of sight.

The reliability determination unit 30 may determine the reliability of the second line of sight as follows. For example, when the difference between the first line of sight and the second line of sight is larger than a predetermined value, the reliability determination unit 30 determines the reliability of the second line of sight as a value smaller than the reliability of the first line of sight. That is, the reliability determination unit 30 determines the reliability of the second line of sight when the continuity between the first line of sight and the second line of sight does not satisfy a predetermined criterion.

As another example, when the difference between the first line of sight within a first predetermined time before the line-of-sight detection mode is switched and the second line of sight within a second predetermined time after the line-of-sight detection mode is switched is greater than a predetermined value, the reliability determination unit 30 may determine the reliability of the second line of sight as a value smaller than the reliability of the first line of sight. Alternatively, for example, when the second line of sight is not included within a predicted range of the line of sight that is predicted based on the change of the first line of sight within a predetermined time before the line-of-sight detection mode is switched, the reliability determination unit 30 may determine the reliability of the second line of sight as a value smaller than the reliability of the first line of sight.

The line-of-sight direction output unit 40 outputs information on the second line of sight estimated by the line-of-sight estimation unit 20 and the reliability of the second line of sight determined by the reliability determination unit 30.

The line-of-sight information utilization apparatus 120 utilizes the information and the reliability of the second line of sight estimated by the line-of-sight detection apparatus 101. The line-of-sight information utilization apparatus 120 is, for example, a warning apparatus for preventing inattentive driving of the driver.

Any one of the line-of-sight detection apparatus 101, the image acquisition apparatus 110, and the line-of-sight information utilization apparatus 120 may form part of the driver monitoring system mounted on the vehicle.

The line-of-sight detection apparatus 101 includes a processing circuit similar to that of the first embodiment. The processing circuit includes the facial feature detection unit 50, the face direction estimation unit 80, the pupil detection unit 60, the pupil reference position determination unit 70, the estimation target selection unit 10, the line-of-sight estimation unit 20, the reliability determination unit 30, and the line-of-sight direction output unit 40. That is, the functions of the respective units described in the second embodiment are achieved by the processing circuit.

(Operation of Line-of-Sight Detection Apparatus and Line-of-Sight Detection Method)

Figure 8:
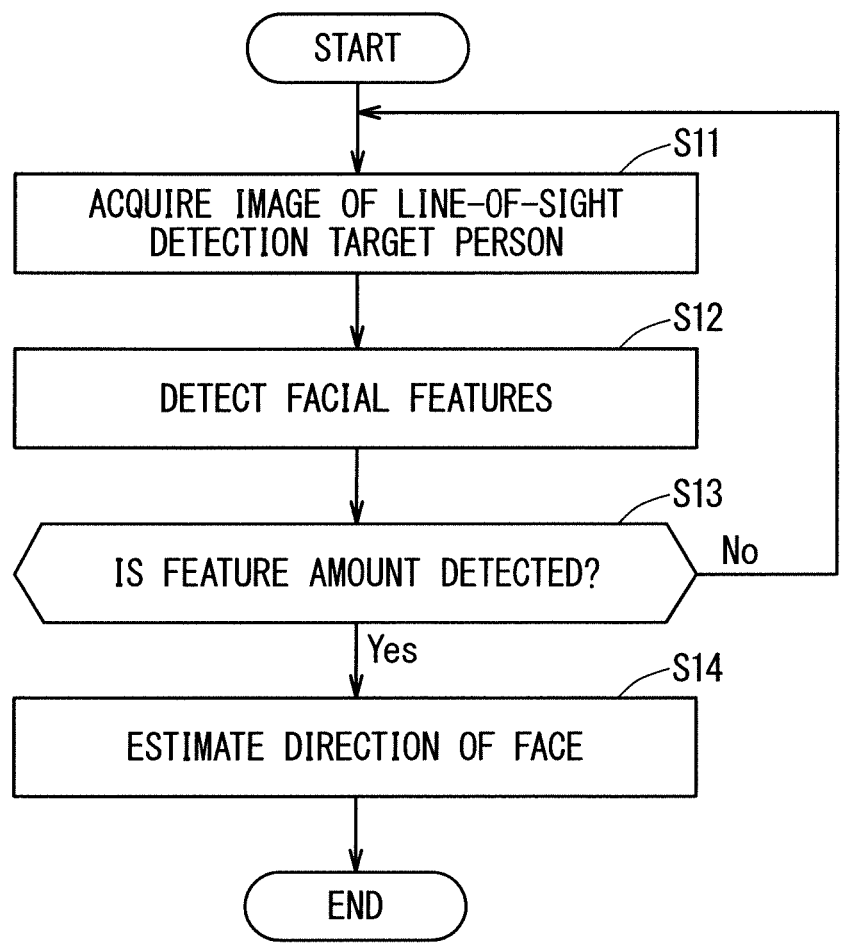
FIG. 8 is a flowchart showing part of an operation of the line-of-sight detection apparatus and a line-of-sight detection method according to the second embodiment.

FIG. 8 is a flowchart showing part of an operation of the line-of-sight detection apparatus 101 and a line-of-sight detection method according to the second embodiment. More specifically, FIG. 8 is a flowchart showing a method for estimating the direction of the face of the line-of-sight detection target person.

In step S11, the image acquisition apparatus 110 acquires an image of the line-of-sight detection target person. Here, the image acquisition apparatus 110 captures an image around the face of the driver 3.

In step S12, the facial feature detection unit 50 detects facial features based on the image around the face. Here, the facial feature detection unit 50 acquires information on the face and face parts based on the image around the face of the driver 3.

In step S13, the facial feature detection unit 50 determines whether or not the feature amount has been able to be detected. If the facial feature detection unit 50 determines that the feature amount has been able to be detected, step S14 is executed. If the facial feature detection unit 50 determines that the feature amount has not been able to be detected, step S11 is executed again. Here, the facial feature detection unit 50 determines whether or not the information on the face and face parts of the driver 3 has been able to be acquired.

In step S14, the face direction estimation unit 80 estimates the direction of the face. Here, the face direction estimation unit 80 estimates the face direction of the driver 3 based on the information on the face and face parts of the driver 3.

Figure 9:
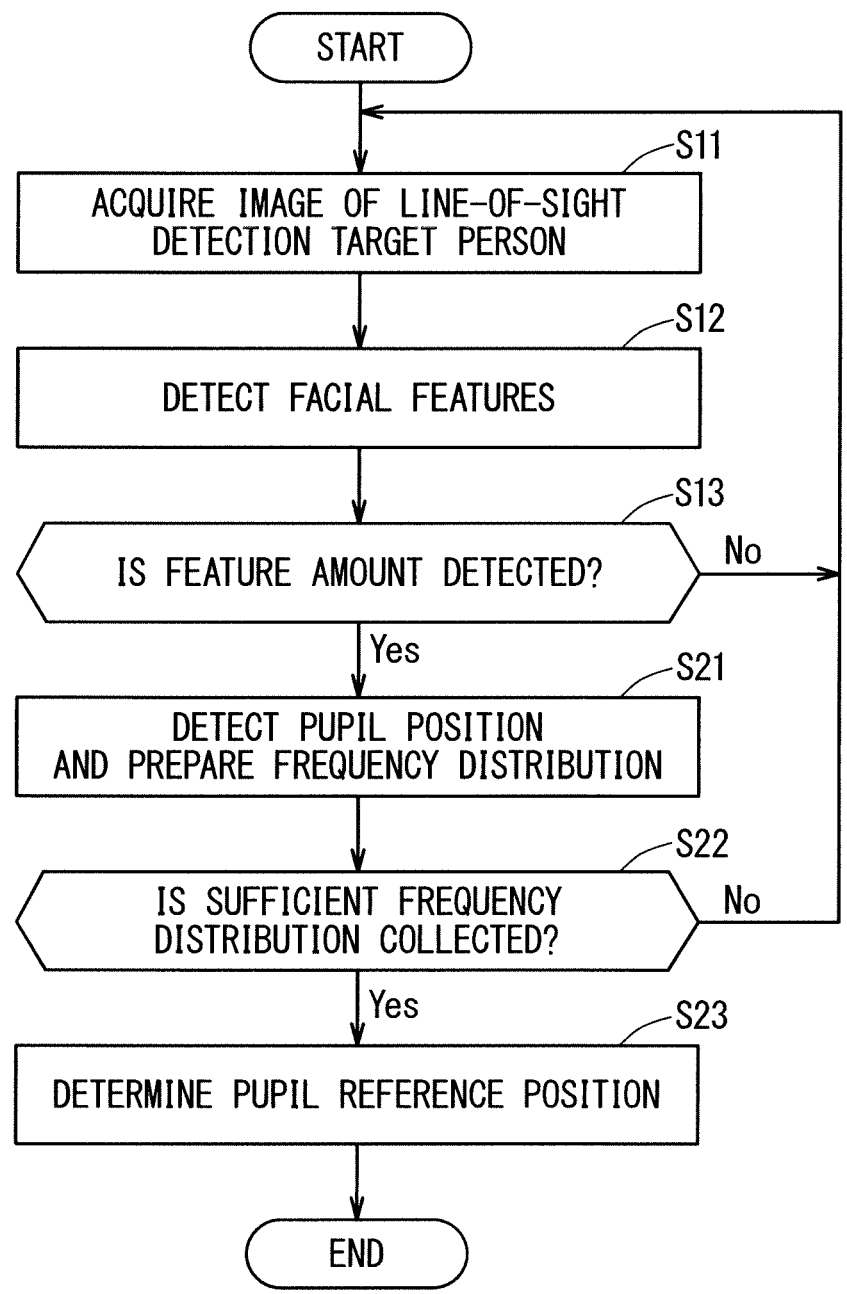
FIG. 9 is a flowchart showing part of an operation of the line-of-sight detection apparatus and a line-of-sight detection method according to the second embodiment.

FIG. 9 is a flowchart showing part of the operation of the line-of-sight detection apparatus 101 and the line-of-sight detection method according to the second embodiment. More specifically, FIG. 9 is a flowchart showing a method for determining the pupil reference position.

Since steps S11 to S13 are the same as the respective steps in FIG. 8, their description will be omitted. However, if it is determined in step S13 that the facial feature detection unit 50 has been able to detect the feature amount, step S21 is executed.

In step S21, the pupil detection unit 60 detects the pupil position based on the information on the face and face parts, and the pupil reference position determination unit 70 prepares a frequency distribution.

In step S22, the pupil reference position determination unit 70 determines whether or not a frequency distribution sufficient to determine the pupil reference position has been collected. If it is determined that a sufficient frequency distribution has been collected, step S23 is executed. If it is determined that a sufficient frequency distribution has not been collected, step S11 is executed again. This determination condition is determined by the number of plots of the frequency distribution, the execution time of the frequency distribution, and the like.

In step S23, the pupil reference position determination unit 70 determines the pupil reference position. At this time, the pupil reference position determination unit 70 calculates, based on the frequency distribution of the pupil position, the position where the frequency of existence of the pupil is the highest, then determines the position as the pupil reference position of the driver 3. Although the pupil position at the time of visually recognizing the front differs from person to person, the line-of-sight estimation apparatus can determine the pupil reference position corresponding to the individual's characteristics by the method for determining the pupil reference position.

Figure 10:
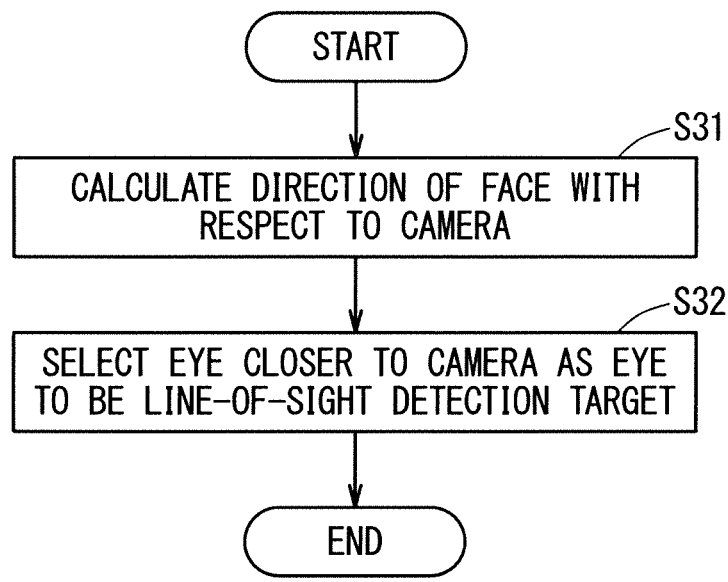
FIG. 10 is a flowchart showing part of an operation of the line-of-sight detection apparatus and a line-of-sight detection method according to the second embodiment.

FIG. 10 is a flowchart showing part of the operation of the line-of-sight detection apparatus 101 and the line-of-sight detection method according to the second embodiment. More specifically, FIG. 10 is a flowchart showing a method for selecting the line-of-sight detection mode.

In step S31, the estimation target selection unit 10 calculates the direction of the face with respect to the camera 2.

In step S32, the estimation target selection unit 10 selects an eye closer to the camera 2 as the eye to be the line-of-sight detection target.

Figure 11:
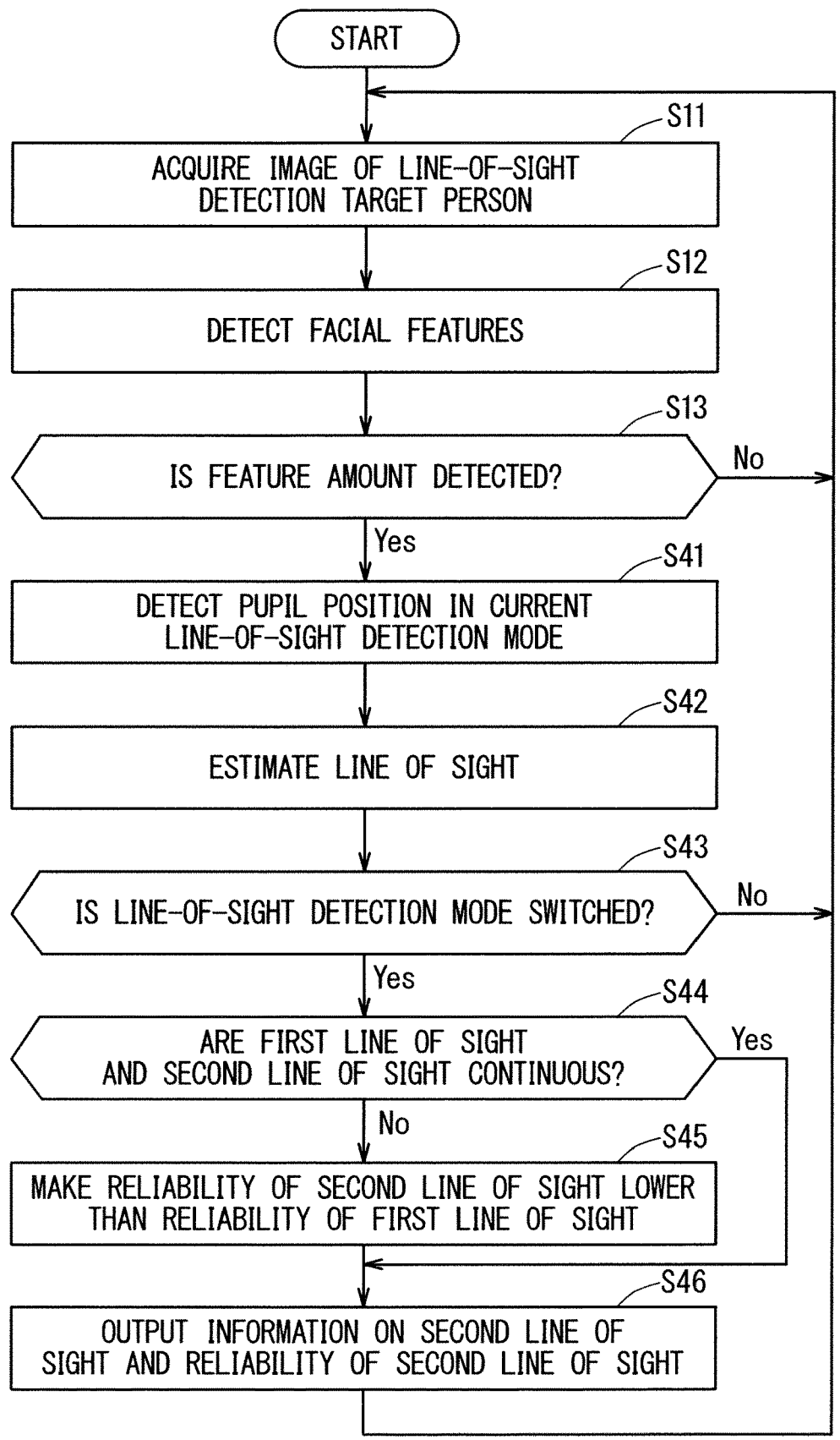
FIG. 11 is a flowchart showing part of an operation of the line-of-sight detection apparatus and a line-of-sight detection method according to the second embodiment.

FIG. 11 is a flowchart showing part of the operation of the line-of-sight detection apparatus 101 and the line-of-sight detection method according to the second embodiment. More specifically, FIG. 11 is a flowchart showing a method for determining the reliability of the line of sight.

Since steps S11 to S13 are the same as the respective steps in FIG. 8, their description will be omitted. However, if it is determined in step S13 that the facial feature detection unit 50 has been able to detect the feature amount, step S41 is executed.

In step S41, the line-of-sight estimation unit 20 detects the pupil position in the current line-of-sight detection mode. For example, when the line-of-sight detection mode is the left eye, the line-of-sight estimation unit 20 detects the pupil position of the left eye.

In step S42, the line-of-sight estimation unit 20 estimates the line of sight. For example, the line-of-sight estimation unit 20 estimates the line of sight from the relationship between the pupil reference position of the left eye determined in step S23 and the pupil position of the left eye detected in step S41.

In step S43, the reliability determination unit 30 determines whether the line-of-sight detection mode has been switched. That is, the reliability determination unit 30 determines whether or not the current line-of-sight detection mode and the line-of-sight detection mode at the time of the previous detection are different. The line-of-sight detection mode at the time of the previous detection and the line of sight estimated in the line of sight detection mode at the time of the previous detection are stored in a storage unit (not shown) of the line-of-sight detection apparatus 101, for example. The reliability determination unit 30 reads the line-of-sight detection mode at the time of the previous detection from the storage unit and makes the above determination. If it is determined that the line-of-sight detection mode has been switched, step S44 is executed. If it is determined that the line-of-sight detection mode has not been switched, step S11 is executed again.

In step S44, the reliability determination unit 30 determines whether or not the first line of sight before the line-of-sight detection mode is switched and the second line of sight after the line-of-sight detection mode is switched are continuous. If it is determined that the first line of sight and the second line of sight are not continuous, step S45 is executed. If it is determined that the first line of sight and the second line of sight are continuous, step S46 is executed.

In step S45, the reliability determination unit 30 determines the reliability of the second line of sight to be a value smaller than the reliability of the first line of sight. That is, the reliability determination unit 30 makes the reliability of the second line of sight lower than the reliability of the first line of sight.

In step S46, the line-of-sight direction output unit 40 outputs the information on the second line of sight and the reliability of the second line of sight. In addition, the information on the second line of sight may include the direction of the face estimated in step S14.

(Reliability Determination Method)

Figure 12:
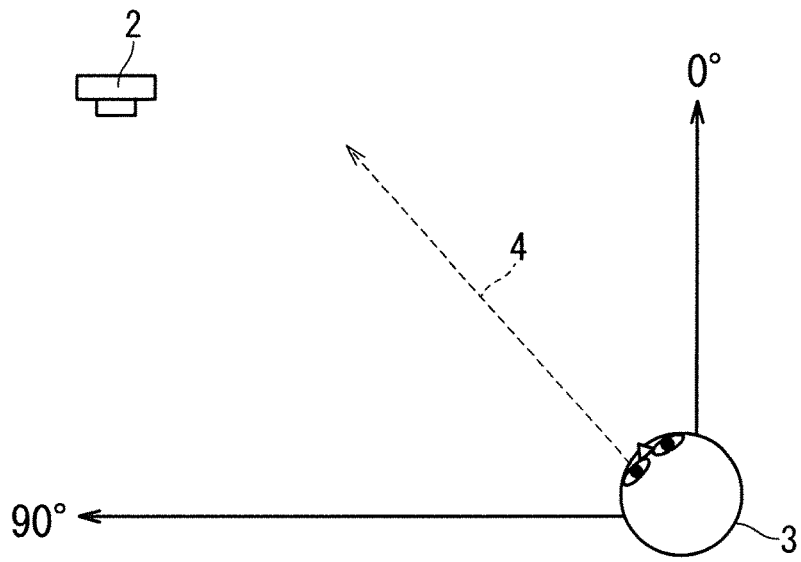
FIG. 12 is a diagram showing an example of a positional relationship between a line-of-sight detection target person and a camera according to the second embodiment.

FIG. 12 is a diagram showing an example of the positional relationship between the driver 3 that is the line-of-sight detection target person and the camera 2 according to the second embodiment. The 0° direction in FIG. 12 is the front direction (in front of the vehicle 1). When the vehicle 1 is a right-hand drive vehicle, the 90° direction is a direction in which the passenger seat is positioned. As described above, the camera 2 is installed near the center console of the vehicle 1. In FIG. 12, the left eye is selected as the line-of-sight detection mode, then the line-of-sight of the left eye is estimated.

FIGS. 13 to 16 are diagrams showing the line-of-sight estimation results according to the second embodiment. As time passes, the line of sight of the driver 3 moves in the direction from 0° to 90°. At time T1, the line-of-sight detection mode is switched. For example, here, the line-of-sight detection mode is switched from the left eye to the right eye or from the left eye to both eyes. In each figure, the black mark is the first line of sight and the white mark is the second line of sight. Hereinafter, the data on one line of sight will be described as a line of sight estimated based on one image.

Figure 13:
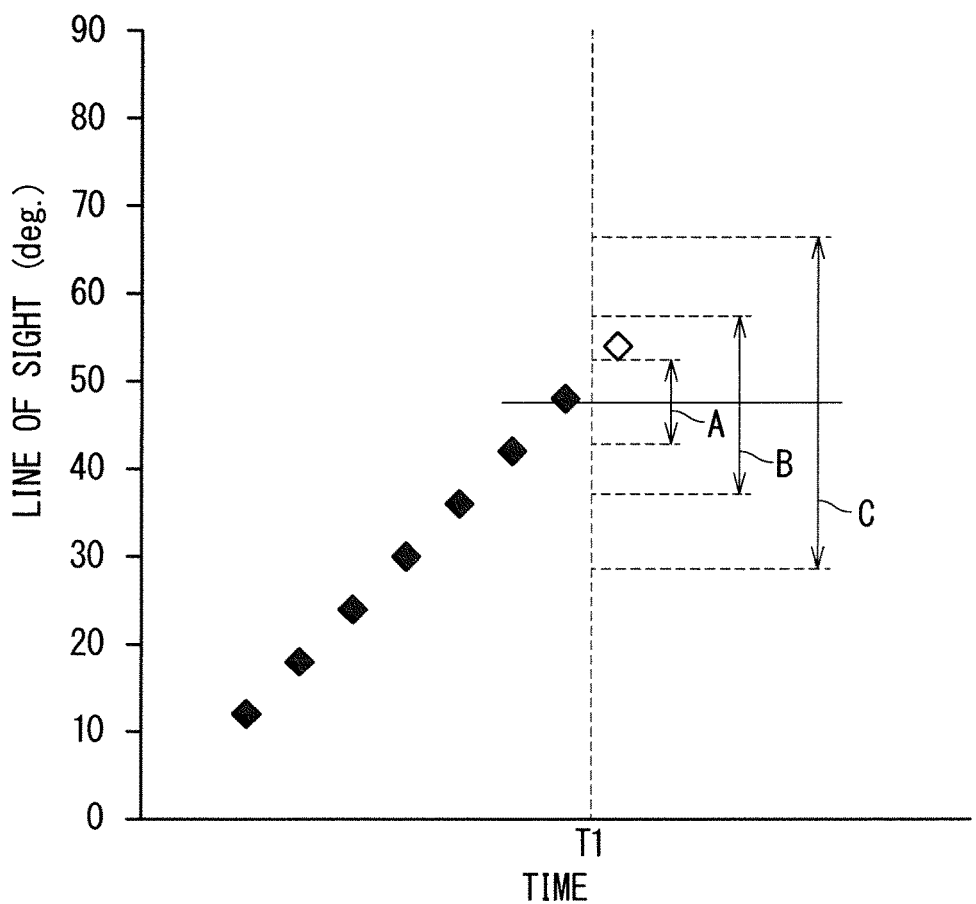
FIG. 13 is a diagram showing a line-of-sight estimation result according to the second embodiment.

In FIG. 13, when the difference between the first line of sight and the second line of sight is larger than a predetermined value, the reliability determination unit 30 determines the reliability of the second line of sight as a value smaller than the reliability of the first line of sight. For example, when the second line of sight is included in a predetermined range A with reference to the first line of sight before the line-of-sight detection mode is switched, the reliability determination unit 30 determines the reliability to be 1.0. In addition, when the second line of sight is included in a predetermined range B, the reliability determination unit 30 determines the reliability to be 0.8. When the second line of sight is included in a predetermined range C, the reliability determination unit 30 determines the reliability to be 0.5. When the second line of sight is positioned outside the predetermined range C, the reliability determination unit 30 determines the reliability to be 0. By this method, the reliability determination unit 30 can determine the reliability of the line of sight based on the continuity between the first line of sight and the second line of sight.

Figure 14:
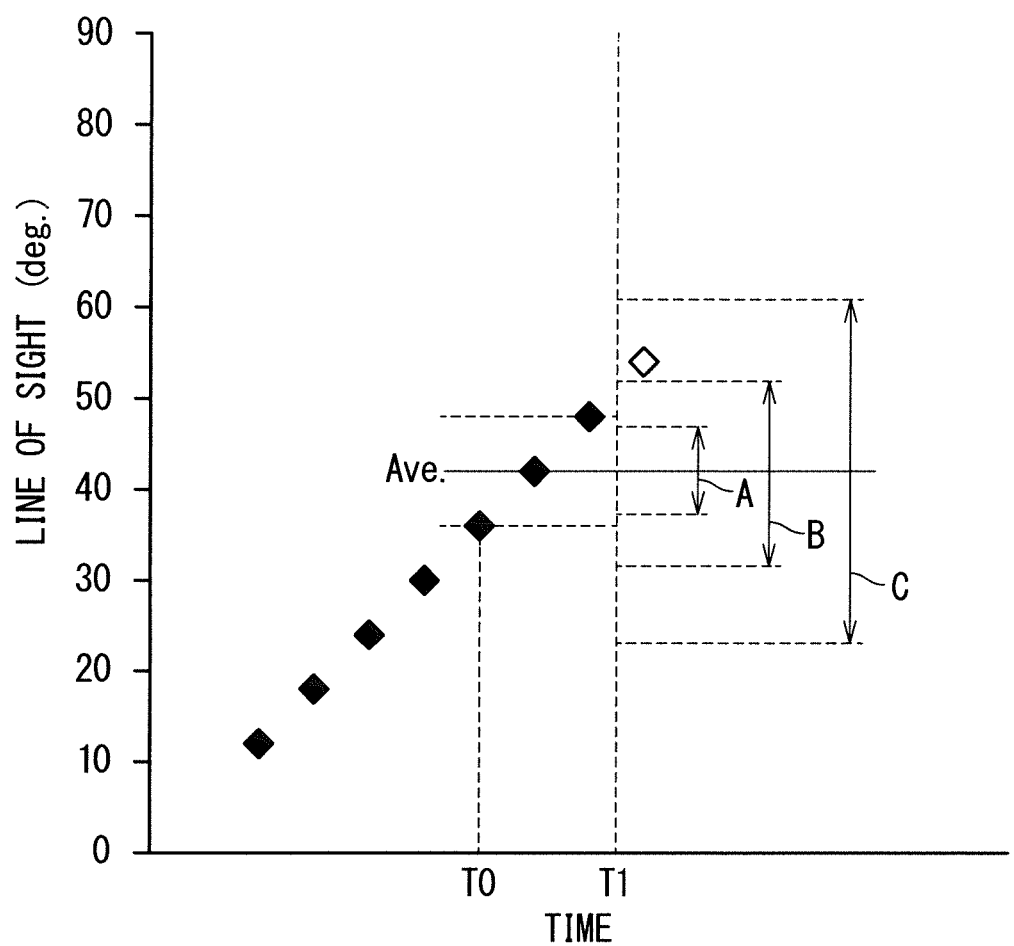
FIG. 14 is a diagram showing a line-of-sight estimation result according to the second embodiment.

In FIG. 14, the first line of sight is an average value of the lines of sight within a first predetermined time. The first predetermined time is a period from time T0 to time T1 before the line-of-sight detection mode is switched. The first line of sight is calculated as an average value of the three lines of sight in the first time. That is, when the difference between the average value of the lines of sight within the first predetermined time and the second line of sight is larger than a predetermined value, the reliability determination unit 30 determines the reliability of the second line of sight to be a value smaller than the reliability of the first line of sight.

Figure 15:
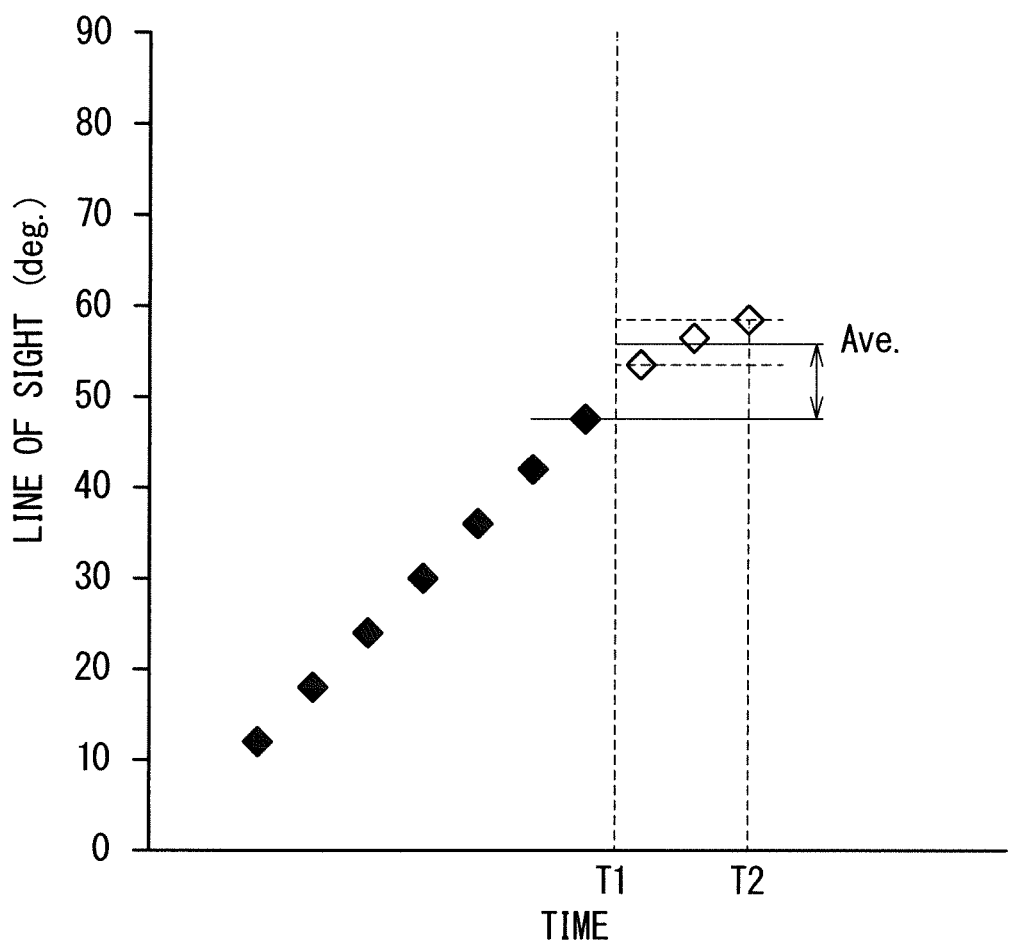
FIG. 15 is a diagram showing a line-of-sight estimation result according to the second embodiment.

In FIG. 15, the second line of sight is an average value of the lines of sight within a second predetermined time. The second predetermined time is a period from time T1 to T2 after the line-of-sight detection mode is switched. The second line of sight is calculated as an average value of the three lines of sight in the second time. That is, when the difference between the first line of sight and the average value of the lines of sight within the second predetermined time is larger than a predetermined value, the reliability determination unit 30 determines the reliability of the second line of sight to be a value smaller than the reliability of the first line of sight.

In addition, although not shown, if the difference between the first line of sight which is the average value of the lines of sight within the first predetermined time and the second line of sight which is the average value of the lines of sight within the second predetermined time is larger than a predetermined value, the reliability of the second line of sight may be determined to be a value smaller than the reliability of the first line of sight.

Figure 16:
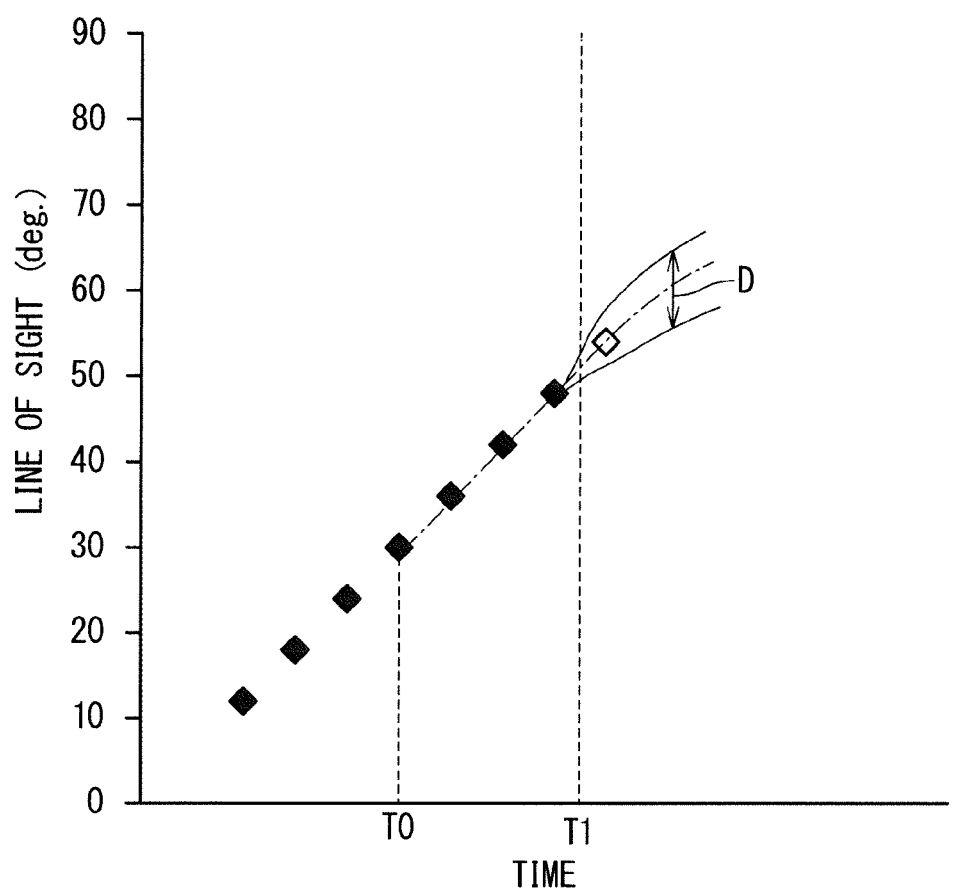
FIG. 16 is a diagram showing a line-of-sight estimation result according to the second embodiment.

In FIG. 16, when the second line of sight is not included within a predicted range D of the line of sight that is predicted based on the change of the first line of sight within a predetermined time before the line-of-sight detection mode is switched, the reliability determination unit 30 may determine the reliability of the second line of sight as a value smaller than the reliability of the first line of sight. In FIG. 16, the predetermined time is a period from time T0 to T1 before the line-of-sight detection mode is switched. When the predicted range D of the line of sight includes the second line of sight, the reliability determination unit 30 determines the reliability to be 1.0, for example. When the second line of sight is positioned outside the predicted range D of the line of sight, the reliability determination unit 30 determines the reliability to be a value smaller than 1.0.

Modification of Second Embodiment

Between step S42 and step S43, the reliability determination unit 30 may determine a first reliability that is the reliability regarding the line of sight estimated in step S42. After that, in step S45, the reliability determination unit 30 may determine the reliability of the second line of sight to be a value smaller than the reliability of the first line of sight by determining a second reliability for correcting the first reliability regarding the second line of sight. That is, the reliability determination unit 30 may lower the reliability of the second line of sight to be lower than the reliability of the first line of sight by correcting the first reliability of the second line of sight with the second reliability.

In step S46, the line-of-sight direction output unit 40 outputs the information on the second line of sight and the corrected reliability of the second line of sight. In addition, the information on the second line of sight may include the direction of the face estimated in step S14.

To summarize the above, when the difference between the first line of sight and the second line of sight is larger than a predetermined value, the reliability determination unit 30 of the line-of-sight detection apparatus 101 according to the second embodiment determines the reliability of the second line of sight to be a value smaller than the reliability of the first line of sight.

With this configuration, the line-of-sight detection apparatus 101 enables highly accurate line-of-sight detection by lowering the reliability of the line of sight when the continuity of each line of sight before and after the switching of the line-of-sight detection mode is not maintained.

In addition, in the line-of-sight detection apparatus 101 according to the second embodiment, the first line of sight may be an average value of the lines of sight within a first predetermined time before the line-of-sight detection mode is switched.

With this configuration, the line-of-sight detection apparatus 101 enables highly accurate line-of-sight detection by lowering the reliability of the line of sight when the continuity of each line of sight before and after the switching of the line-of-sight detection mode is not maintained. Since the reliability can be determined by the average value of the lines of sight, the accuracy of the reliability determination is improved.

In addition, in the line-of-sight detection apparatus 101 according to the second embodiment, the second line of sight may be an average value of the lines of sight within a second predetermined time after the line-of-sight detection mode has been switched.

With this configuration, the line-of-sight detection apparatus 101 enables highly accurate line-of-sight detection by lowering the reliability of the line of sight when the continuity of each line of sight before and after the switching of the line-of-sight detection mode is not maintained. Since the reliability can be determined by the average value of the lines of sight, the accuracy of the reliability determination is improved.

In addition, when the second line of sight is not included within a predicted range of the line of sight that is predicted based on the change of the first line of sight within a predetermined time before the line-of-sight detection mode is switched, the reliability determination unit 30 of the line-of-sight detection apparatus 101 according to the second embodiment may determine the reliability of the second line of sight as a value smaller than the reliability of the first line of sight.

With this configuration, the line-of-sight detection apparatus 101 enables highly accurate line-of-sight detection by lowering the reliability of the line of sight when the continuity of each line of sight before and after the switching of the line-of-sight detection mode is not maintained. Since it is possible to predict the continuity of the second line of sight, the accuracy of reliability determination is improved.

In addition, the reliability determination unit 30 of the line-of-sight detection apparatus 101 according to the second embodiment determines the reliability of the second line of sight when the line-of-sight detection mode is switched from the right eye to the left eye or from the left eye to the right eye.

With this configuration, the line-of-sight detection apparatus 101 enables highly accurate line-of-sight detection before and after the switching of the line-of-sight detection mode even when the pupil reference position of each of the left and right eyes is different.

In addition, the reliability determination unit 30 of the line-of-sight detection apparatus 101 according to the second embodiment may determine the reliability of the second line of sight when the line-of-sight detection mode is switched from both eyes to one eye or from one eye to both eyes.

With this configuration, the line-of-sight detection apparatus 101 enables highly accurate line-of-sight detection before and after the switching of the line-of-sight detection mode even when the pupil reference position of each of the left and right eyes is different.

In addition, the line-of-sight detection apparatus 101 according to the second embodiment further includes the facial feature detection unit 50 that acquires an image of the line-of-sight detection target person and detects facial features of the line-of-sight detection target person based on the image, and the face direction estimation unit 80 that estimates the direction of the face of the line-of-sight detection target person based on the facial features. The estimation target selection unit 10 selects the line-of-sight detection mode based on the direction of the face of the line-of-sight detection target person.

With this configuration, the line-of-sight detection apparatus 101 enables highly accurate line-of-sight detection.

In addition, the line-of-sight detection apparatus 101 according to the second embodiment further includes the pupil detection unit 60 that detects the position of the pupil based on the facial features, and the pupil reference position determination unit 70 that determines, based on the pupil position, the pupil reference position that is the pupil position when the line-of-sight detection target person visually recognize the front. The line-of-sight estimation unit 20 estimates the line of sight of the line-of-sight detection target person based on the difference between the pupil position in the line-of-sight detection mode selected by the estimation target selection unit 10 and the pupil reference position.

With this configuration, the line-of-sight detection apparatus 101 enables highly accurate line-of-sight detection.

Third Embodiment

The line-of-sight detection apparatus shown in each embodiment can also be applied to a system constructed by appropriately combining a navigation apparatus, a communication terminal, a server, and the functions of applications installed in these. Here, the navigation apparatus includes, for example, a portable navigation device (PND) and the like. The communication terminal includes a mobile terminal such as a mobile phone, a smartphone, and a tablet.

Figure 17:
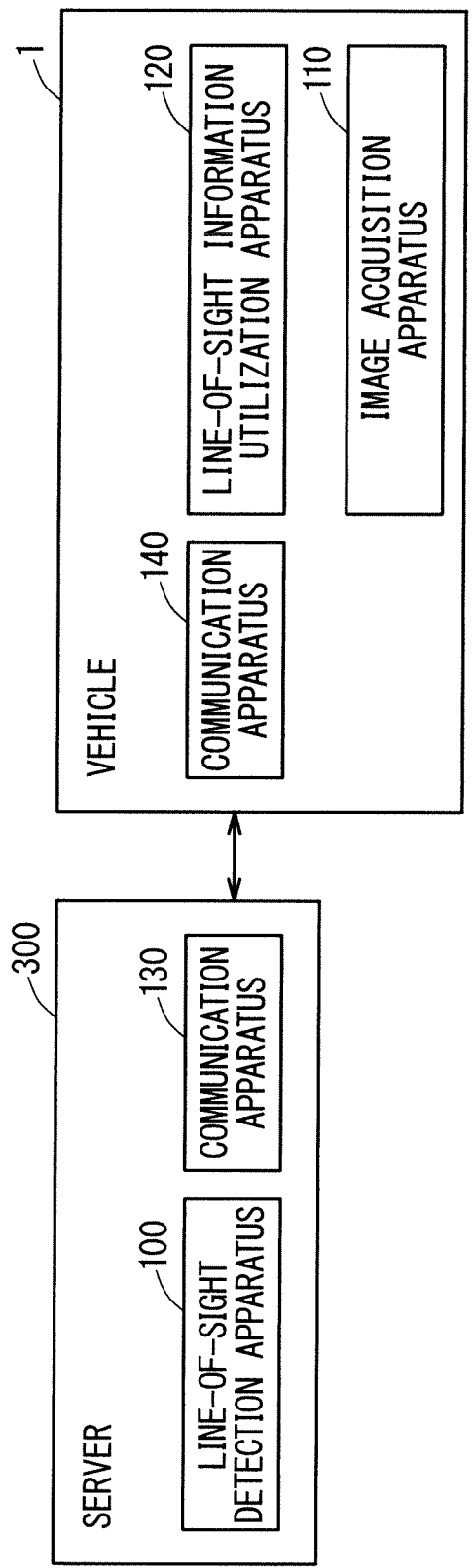
FIG. 17 is a block diagram showing a configuration of a line-of-sight detection apparatus and apparatuses that operate in connection therewith according to the third embodiment.

FIG. 17 is a block diagram showing a configuration of a line-of-sight detection apparatus 100 and apparatuses that operate in connection therewith according to the third embodiment.

A line-of-sight detection apparatus 100 and a communication apparatus 130 are provided in the server 300. The line-of-sight detection apparatus 100 acquires an image of the line-of-sight detection target person from the image acquisition apparatus 110 provided in the vehicle 1 via the communication apparatus 140 and the communication apparatus 130. The line-of-sight detection apparatus 100 outputs the information on the second line-of-sight after the line-of-sight detection mode is switched and the reliability of the second line-of-sight to the line-of-sight information utilization apparatus 120 via each communication apparatus.

Thus, arranging the line-of-sight detection apparatus 100 in the server 300 allows the configuration of the in-vehicle apparatus to be simplified. In addition, similarly, since the results of a large number of line-of-sight estimation can be accumulated and learned, the accuracy of line-of-sight estimation and reliability determination is improved.

In addition, the functions or components of the line-of-sight detection apparatus 100 may be arranged in a distributed manner, such as some of them are provided in the server 300 and others are provided in the vehicle 1.

It should be noted that in the present invention, each embodiment can be freely combined, and each embodiment can be appropriately modified, or omitted within the scope of the present invention.

Although the present invention is described in detail, the above description is, in all aspects, illustrative, and the present invention is not limited to the above description. It is understood that innumerable modifications not illustrated can be envisaged without departing from the scope of the present invention.

EXPLANATION OF REFERENCE SIGNS

1: vehicle
2: camera
3: driver
10: estimation target selection unit
20: line-of-sight estimation unit
30: reliability determination unit
40: line-of-sight direction output unit
50: facial feature detection unit
60: pupil detection unit
70: pupil reference position determination unit
80: face direction estimation unit
100: line-of-sight detection apparatus

The invention claimed is:

1. A line-of-sight detection apparatus comprising:
estimation target selection circuitry to select an eye to be a line-of-sight estimation target of a line-of-sight detection target person as one line-of-sight detection mode in a plurality of switchable line-of-sight detection modes;
line-of-sight estimation circuitry to estimate a line of sight of the line-of-sight detection target person in the one line-of-sight detection mode;
reliability determination circuitry to determine, based on a first line of sight that is the line of sight before the line-of-sight detection mode is switched by selection of the estimation target selection circuitry and a second line of sight that is the line of sight after the line-of-sight detection mode is switched, reliability of the second line of sight after the line-of-sight detection mode is switched; and
line-of-sight direction output circuitry to output information on the second line of sight and the reliability of the second line of sight.

2. The line-of-sight detection apparatus according to claim 1, wherein the reliability determination circuitry determines the reliability of the second line of sight to be a value smaller than reliability of the first line of sight when a difference between the first line of sight and the second line of sight is larger than a predetermined value.

3. The line-of-sight detection apparatus according to claim 1, wherein the first line of sight is an average value of the lines of sight within a first predetermined time before the line-of-sight detection mode is switched.

4. The line-of-sight detection apparatus according to claim 1, wherein the second line of sight is an average value of the lines of sight within a second predetermined time after the line-of-sight detection mode is switched.

5. The line-of-sight detection apparatus according to claim 1, wherein the reliability determination circuitry determines the reliability of the second line of sight to be a value smaller than reliability of the first line of sight when the second line of sight is not included within a predicted range of the line of sight that is predicted based on a change of the first line of sight within a predetermined time before the line-of-sight detection mode is switched.

6. The line-of-sight detection apparatus according to claim 1, wherein the reliability determination circuitry determines the reliability of the second line of sight when the line-of-sight detection mode is switched from a right eye to a left eye or from a left eye to a right eye.

7. The line-of-sight detection apparatus according to claim 1, wherein the reliability determination circuitry determines the reliability of the second line of sight when the line-of-sight detection mode is switched from both eyes to one eye or from one eye to both eyes.

8. The line-of-sight detection apparatus according to claim 1, further comprising:
facial feature detection circuitry configured to acquire an image of the line-of-sight detection target person and detect facial features of the line-of-sight detection target person based on the image; and
face direction estimation circuitry configured to estimate a direction of a face of the line-of-sight detection target person based on the facial features, wherein
the estimation target selection circuitry selects the one line-of-sight detection mode based on the direction of the face of the line-of-sight detection target person.

9. The line-of-sight detection apparatus according to claim 8, further comprising:
pupil detection circuitry configured to detect a pupil position based on the facial features; and
pupil reference position determination circuitry configured to determine, based on the pupil position, a pupil reference position that is the pupil position when the line-of-sight detection target person visually recognize a front, wherein
the line-of-sight estimation circuitry estimates the line of sight of the line-of-sight detection target person based on a difference between the pupil position in the one line-of-sight detection mode selected by the estimation target selection circuitry and the pupil reference position.

10. A line-of-sight detection method comprising:
selecting an eye to be a line-of-sight estimation target of a line-of-sight detection target person as one line-of-sight detection mode in a plurality of switchable line-of-sight detection modes;
estimating a line of sight of the line-of-sight detection target person in the one line-of-sight detection mode;
determining, based on a first line of sight that is the line of sight before the line-of-sight detection mode is switched and a second line of sight that is the line of sight after the line-of-sight detection mode is switched, reliability of the second line of sight after the line-of-sight detection mode is switched; and
outputting information on the second line of sight and the reliability of the second line of sight.

* * * * *